United States Patent
Dota

(10) Patent No.: US 10,070,646 B2
(45) Date of Patent: *Sep. 11, 2018

(54) TETRAZOLINONE COMPOUND AND APPLICATION THEREOF

(71) Applicant: SUMITOMO CHEMICAL COMPANY, LIMITED, Tokyo (JP)

(72) Inventor: Koichiro Dota, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 53 days.

This patent is subject to a terminal disclaimer.

(21) Appl. No.: 15/128,703

(22) PCT Filed: Mar. 23, 2015

(86) PCT No.: PCT/JP2015/059818
§ 371 (c)(1),
(2) Date: Sep. 23, 2016

(87) PCT Pub. No.: WO2015/147313
PCT Pub. Date: Oct. 1, 2015

(65) Prior Publication Data
US 2017/0118983 A1    May 4, 2017

(30) Foreign Application Priority Data

Mar. 28, 2014  (JP) .................................. 2014-067943

(51) Int. Cl.
*A01N 43/713*    (2006.01)
*C07D 403/12*    (2006.01)
*C07D 401/14*    (2006.01)

(52) U.S. Cl.
CPC ......... *A01N 43/713* (2013.01); *C07D 401/14* (2013.01); *C07D 403/12* (2013.01)

(58) Field of Classification Search
None
See application file for complete search history.

(56) References Cited

U.S. PATENT DOCUMENTS

| | | | |
|---|---|---|---|
| 5,589,439 A | 12/1996 | Goto et al. | |
| 5,641,727 A | 6/1997 | Goto et al. | |
| 5,861,359 A | 1/1999 | Theodoridis | |
| 6,294,503 B1 | 9/2001 | Gupta et al. | |
| 6,583,090 B1 | 6/2003 | Gewehr et al. | |
| 2014/0323305 A1 | 10/2014 | Rheinheimer et al. | |
| 2015/0031733 A1 | 1/2015 | Yoshimoto et al. | |
| 2015/0051171 A1 | 2/2015 | Yoshimoto et al. | |
| 2015/0203511 A1 | 7/2015 | Arimori et al. | |
| 2015/0223460 A1 | 8/2015 | Arimori et al. | |
| 2015/0299146 A1 | 10/2015 | Hasegawa et al. | |
| 2015/0336908 A1 | 11/2015 | Shioda et al. | |
| 2016/0081339 A1 | 3/2016 | Yoshimoto et al. | |
| 2016/0081340 A1 | 3/2016 | Arimori et al. | |
| 2016/0150787 A1 | 6/2016 | Azuma et al. | |
| 2016/0157489 A1 | 6/2016 | Shioda et al. | |
| 2016/0159755 A1 | 6/2016 | Shioda et al. | |
| 2016/0174558 A1 | 6/2016 | Hou et al. | |
| 2016/0205935 A1 | 7/2016 | Akioka et al. | |
| 2016/0249617 A1 | 9/2016 | Dota | |
| 2016/0272622 A1 | 9/2016 | Azuma et al. | |
| 2016/0311775 A1 | 10/2016 | Shioda et al. | |

FOREIGN PATENT DOCUMENTS

| | | |
|---|---|---|
| CN | 12875540 A | 1/2013 |
| EP | 0 902 028 A1 | 3/1999 |
| JP | 8-81459 A | 3/1996 |
| JP | 8-99975 A | 4/1996 |
| JP | 9-87281 A | 3/1997 |
| JP | 9-100277 A | 4/1997 |
| JP | 9-110863 A | 4/1997 |
| JP | 9-208565 A | 8/1997 |

(Continued)

OTHER PUBLICATIONS

International Search Report issued in PCT/JP2015/059818, dated Apr. 28, 2015.
English translation of the International Search Report (Form PCT/ISA/237) for International Application No. PCT/JP2014/078005, dated Nov. 25, 2014.
Extended European Search Report, dated Jul. 10, 2017, for European Application No. 15770001.4.

*Primary Examiner* — Alicia L Otton
(74) *Attorney, Agent, or Firm* — Birch, Stewart, Kolasch & Birch, LLP

(57) ABSTRACT

A tetrazolinone compound represented by formula (1):

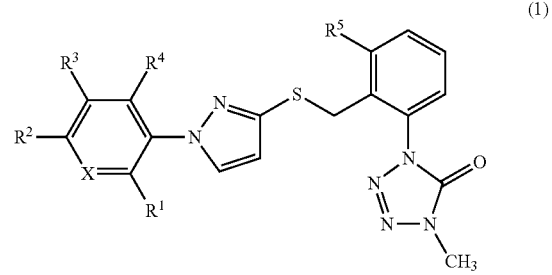

(1)

wherein X represents $CR^6$ or a nitrogen atom, $R^1$, $R^2$, $R^3$, $R^4$, and $R^6$ each independently represents a halogen atom, a C1-C4 alkyl group optionally having one or more halogen atoms, etc., and $R^5$ represents a C1-C4 alkyl group optionally having one or more halogen atoms, a C3-C4 cycloalkyl group optionally having one or more halogen atoms, etc., has excellent control activity against pests.

6 Claims, No Drawings

(56) References Cited

FOREIGN PATENT DOCUMENTS

| | | |
|---|---|---|
| JP | 11-152278 A | 6/1999 |
| JP | 2001-512460 A | 8/2001 |
| WO | WO 96/38229 A1 | 11/1996 |
| WO | 9-100272 A | 4/1997 |
| WO | WO 98/25912 A1 | 6/1998 |
| WO | WO 98/35961 A1 | 8/1998 |
| WO | WO 98/51683 A1 | 11/1998 |
| WO | WO 99/46246 A1 | 9/1999 |
| WO | WO 99/48890 A1 | 9/1999 |
| WO | WO 2013/092224 A1 | 6/2013 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2014/192953 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/050039 A1 | 4/2015 |
| WO | WO 2015/050040 A1 | 4/2015 |
| WO | WO 2015/058806 A1 | 4/2015 |
| WO | WO 2015/060461 A1 | 4/2015 |
| WO | 2015/088038 A1 | 6/2015 |
| WO | WO 2015/147314 A1 | 10/2015 |
| WO | WO 2015/147336 A1 | 10/2015 |

TETRAZOLINONE COMPOUND AND APPLICATION THEREOF

TECHNICAL FIELD

The present invention relates to a tetrazolinone compound and application thereof.

BACKGROUND ART

Heretofore, various chemicals have been developed so as to control pests and provided in practice use, but in some cases, these chemicals may not exert enough activity.

Meanwhile, there have been known, as compounds for controlling pests, compounds having a tetrazolinone ring represented by the following formula (A):

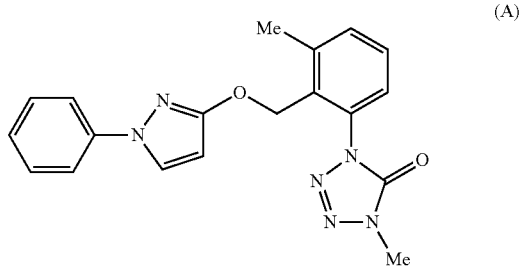 [SMILES: Cc1cccc(-n2nnn(C)c2=O)c1COc1ccn(-c2ccccc2)n1]

(A)

(see WO 2013/162072 A).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus leading to the present invention.

The present invention includes the followings [1] to [4].
[1] A tetrazolinone compound represented by formula (1):

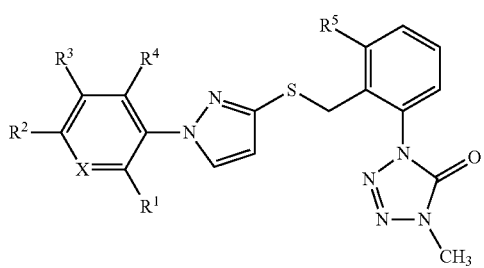

(1)

wherein X represents $CR^6$ or a nitrogen atom,
$R^1$, $R^2$, $R^3$, $R^4$, and $R^6$ each independently represents a halogen atom, a hydrogen atom, a cyano group, a C1-C4 alkyl group optionally having one or more halogen atoms, or a C1-C4 alkoxy group optionally having one or more halogen atoms, and
$R^5$ represents a halogen atom, a C1-C4 alkyl group optionally having one or more halogen atoms, a C3-C4 cycloalkyl group optionally having one or more halogen atoms, or a C1-C4 alkoxy group optionally having one or more halogen atoms.

[2] The tetrazolinone compound according to [1], wherein X is $CR^6$.
[3] The tetrazolinone compound according to [1], wherein X is a nitrogen atom.
[4] The tetrazolinone compound according to [3], wherein $R^3$ and $R^4$ are hydrogen atoms.
[5] A pest control agent comprising the tetrazolinone compound according to any one of [1] to [4].
[6] A method for control pests, which comprises applying an effective amount of the tetrazolinone compound according to any one of [1] to [4] to plants or soil.
[7] Use of the tetrazolinone compound according to any one of [1] to [4] for controlling pests.

According to the present invention, pests can be controlled.

MODE FOR CARRYING OUT THE INVENTION

In the present invention, a tetrazolinone compound represented by formula (1) is referred to as the present compound, and a pest control agent containing the present compound is referred to as the present control agent.

Substituents as used herein will be mentioned below.

The halogen atom represents a fluorine atom, a chlorine atom, a bromine atom, and an iodine atom.

Examples of the C1-C4 alkyl group optionally having one or more halogen atoms include a methyl group, an ethyl group, a propyl group, an isopropyl group, a butyl group, an isobutyl group, a sec-butyl group, a tert-butyl group, a fluoromethyl group, a chloromethyl group, a dichloromethyl group, a difluoromethyl group, a trifluoromethyl group, a trichloromethyl group, a 2-fluoroethyl group, a 2,2,2-trifluoroethyl group, and a 1-trifluoromethyl-2,2,2-trifluoroethyl group.

Examples of the C3-C4 cycloalkyl group optionally having one or more halogen atoms include a cyclopropyl group, a cyclobutyl group, a 2,2-dichlorocyclopropyl group, and a 2,2-difluorocyclopropyl group.

Examples of the C1-C4 alkoxy group optionally having one or more halogen atoms include a methoxy group, an ethoxy group, a propyloxy group, an isopropyloxy group, a butyloxy group, a trifluoromethoxy group, a difluoromethoxy group, a 2-fluoroethoxy group, a 2,2,2-trifluoroethoxy group, a 3-chloro propyloxy group, and a 3-chlorobutyloxy group.

Examples of Aspect of the present compound include the following compounds.
A tetrazolinone compound in which $R^5$ is a halogen atom in formula (1).
A tetrazolinone compound in which $R^5$ is a C1-C4 alkyl group optionally having one or more halogen atoms in formula (1).
A tetrazolinone compound in which $R^5$ is a C3-C4 cycloalkyl group optionally having one or more halogen atoms in formula (1).
A tetrazolinone compound in which $R^5$ is a C1-C4 alkoxy group optionally having one or more halogen atoms in formula (1).
A tetrazolinone compound in which $R^1$ is a hydrogen atom in formula (1).
A tetrazolinone compound in which $R^1$ is a halogen atom in formula (1).
A tetrazolinone compound in which $R^1$ is a C1-C4 alkyl group optionally having one or more halogen atoms in formula (1).

A tetrazolinone compound in which R¹ is a C1-C4 alkoxy group optionally having one or more halogen atoms in formula (1).

A tetrazolinone compound in which R² is a hydrogen atom in formula (1).

A tetrazolinone compound in which R² is a halogen atom in formula (1).

A tetrazolinone compound in which R² is a C1-C4 alkyl group optionally having one or more halogen atoms in formula (1).

A tetrazolinone compound in which R² is a C1-C4 alkoxy group optionally having one or more halogen atoms in formula (1).

A tetrazolinone compound in which R³ is a hydrogen atom in formula (1).

A tetrazolinone compound in which R³ is a halogen atom in formula (1).

A tetrazolinone compound in which R³ is a C1-C4 alkyl group optionally having one or more halogen atoms in formula (1).

A tetrazolinone compound in which R⁴ is a hydrogen atom in formula (1).

A tetrazolinone compound in which R⁴ is a halogen atom in formula (1).

A tetrazolinone compound in which R⁴ is a C1-C4 alkyl group optionally having one or more halogen atoms in formula (1).

[Aspect 1]
A tetrazolinone compound represented by formula (1a):

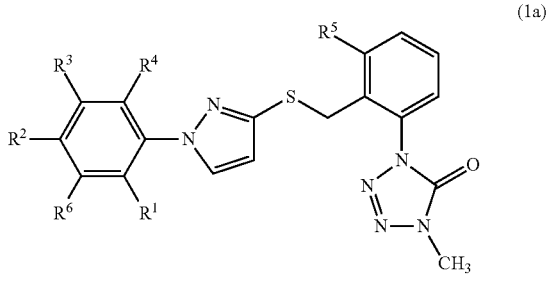

(1a)

wherein symbols are the same as defined above.

A tetrazolinone compound in which R¹ is a C1-C4 alkyl group optionally having one or more halogen atoms, or a hydrogen atom in [Aspect 1].

A tetrazolinone compound in which R¹ is a C1-C4 alkyl group optionally having one or more halogen atoms, a halogen atom, or a C1-C4 alkoxy group optionally having one or more halogen atoms in [Aspect 1].

A tetrazolinone compound in which R¹ is a hydrogen atom or a halogen atom in [Aspect 1].

A tetrazolinone compound in which R² is a C1-C4 alkyl group optionally having one or more halogen atoms, or a hydrogen atom in [Aspect 1].

A tetrazolinone compound in which R² is a C1-C4 alkyl group optionally having one or more halogen atoms, a halogen atom, or a C1-C4 alkoxy group optionally having one or more halogen atoms in [Aspect 1].

A tetrazolinone compound in which R⁵ is a halogen atom in [Aspect 1].

A tetrazolinone compound in which R⁵ is a methyl group in [Aspect 1].

A tetrazolinone compound in which R⁵ is an ethyl group in [Aspect 1].

A tetrazolinone compound in which R⁵ is a methoxy group in [Aspect 1].

A tetrazolinone compound in which R⁵ is a cyclopropyl group in [Aspect 1].

A tetrazolinone compound in which R⁵ is a C1-C4 alkyl group optionally having one or more halogen atoms, R¹ and R² are each independently a hydrogen atom, a halogen atom, a cyano group, or a C1-C4 alkoxy group optionally having one or more halogen atoms, and R³ and R⁴ are each independently a hydrogen atom or a halogen atom in [Aspect 1].

A tetrazolinone compound in which R⁵ is a C1-C4 alkyl group optionally having one or more halogen atoms in [Aspect 1].

A tetrazolinone compound in which R⁵ is a C1-C4 alkyl group optionally having one or more halogen atoms, and R¹, R², R³, R⁴, and R⁶ are each independently a hydrogen atom, a halogen atom, or a C1-C4 alkoxy group optionally having one or more halogen atoms in [Aspect 1].

A tetrazolinone compound in which R⁵ is a C1-C4 alkyl group optionally having one or more halogen atoms, and R¹, R², R³, R⁴, and R⁶ are each independently a hydrogen atom, a halogen atom, or a C1-C4 alkoxy group optionally having one or more halogen atoms in [Aspect 1].

A tetrazolinone compound in which R⁵ is a C1-C4 alkyl group optionally having one or more halogen atoms, R¹ and R⁴ are each independently a hydrogen atom or a C1-C4 alkoxy group optionally having one or more halogen atoms, R³ and R⁶ are hydrogen atoms, and R² is a halogen atom in [Aspect 1].

A tetrazolinone compound in which R⁵ is a C1-C4 alkyl group optionally having one or more halogen atoms, R¹, R³, R⁴, and R⁶ are hydrogen atoms, and R² is a halogen atom in [Aspect 1].

[Aspect 2]
A tetrazolinone compound represented by formula (1b):

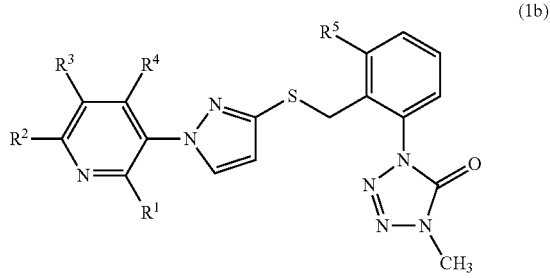

(1b)

wherein symbols are the same as defined above.

A tetrazolinone compound in which R¹ is a C1-C4 alkyl group optionally having one or more halogen atoms, or a hydrogen atom in [Aspect 2].

A tetrazolinone compound in which in R¹ is a C1-C4 alkyl group optionally having one or more halogen atoms, a halogen atom, or a C1-C4 alkoxy group optionally having one or more halogen atoms in [Aspect 2].

A tetrazolinone compound in which R¹ is a hydrogen atom or a halogen atom in [Aspect 2].

A tetrazolinone compound in which R² is a C1-C4 alkyl group optionally having one or more halogen atoms, or a hydrogen atom in [Aspect 2].

A tetrazolinone compound in which R² is a C1-C4 alkyl group optionally having one or more halogen atoms, a halogen atom, or a C1-C4 alkoxy group optionally having one or more halogen atoms in [Aspect 2].

A tetrazolinone compound in which in R⁵ is a halogen atom in [Aspect 2].
A tetrazolinone compound in which R⁵ is a methyl group in [Aspect 2].
A tetrazolinone compound in which R⁵ is an ethyl group in [Aspect 2].
A tetrazolinone compound in which R⁵ is a methoxy group in [Aspect 2].
A tetrazolinone compound in which R⁵ is a cyclopropyl group in [Aspect 2].
A tetrazolinone compound in which R⁵ is a C1-C4 alkyl group optionally having one or more halogen atoms, R¹ and R² are each independently a halogen atom, a cyano group, or a C1-C4 alkoxy group optionally having one or more halogen atoms, and R³ and R⁴ are each independently a halogen atom in [Aspect 2].

[Aspect 3]
A tetrazolinone compound represented by formula (1c):

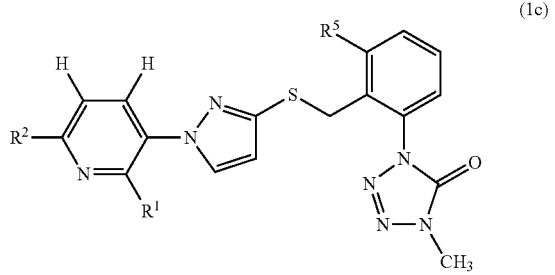

wherein symbols are the same as defined above.
A tetrazolinone compound in which R¹ is a C1-C4 alkyl group optionally having one or more halogen atoms, or a hydrogen atom in [Aspect 3].
A tetrazolinone compound in which R¹ is a C1-C4 alkyl group optionally having one or more halogen atoms, a halogen atom, or a C1-C4 alkoxy group optionally having one or more halogen atoms in [Aspect 3].
A tetrazolinone compound in which R¹ is a hydrogen atom or a halogen atom in [Aspect 3].
A tetrazolinone compound in which R² is a C1-C4 alkyl group optionally having one or more halogen atoms, or a hydrogen atom in [Aspect 3].
A tetrazolinone compound in which R² is a C1-C4 alkyl group optionally having one or more halogen atoms, a halogen atom, or a C1-C4 alkoxy group optionally having one or more halogen atoms in [Aspect 3].
A tetrazolinone compound in which R⁵ is a halogen atom in [Aspect 3].
A tetrazolinone compound in which R⁵ is a methyl group in [Aspect 3].
A tetrazolinone compound in which R⁵ is an ethyl group in [Aspect 3].
A tetrazolinone compound in which R⁵ is a methoxy group in [Aspect 3].
A tetrazolinone compound in which R⁵ is a cyclopropyl group in [Aspect 3].
A tetrazolinone compound in which R⁵ is a C1-C4 alkyl group optionally having one or more halogen atoms, and R¹ and R² are each independently a halogen atom, a cyano group, or a C1-C4 alkoxy group optionally having one or more halogen atoms in [Aspect 3].

Next, a process for producing the present compound will be described.

(Production Process A)
The present compound represented by formula (1) can be produced by reacting a compound represented by formula (A1) (hereinafter referred to as the compound (A1)) with a compound represented by formula (A2) (hereinafter referred to as the compound (A2)) in the presence of a base:

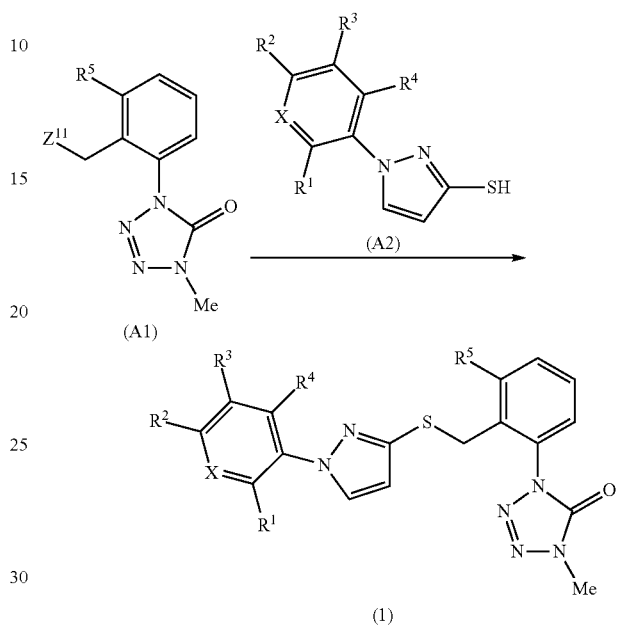

wherein R¹, R², R³, R⁴, R⁵ and X are the same as defined above, and Z¹¹ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.
Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroetane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water, mixtures thereof, and mixtures of water and these solvents.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

The compound (A1) to be used in the reaction is produced in accordance with Reference Production Process A of WO 2013/162072 A.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (A1)

After completion of the reaction, the present compound represented by formula (1) can be isolated by performing post-treatment operations such as extraction of the reaction mixture with an organic solvent, and drying and concentration of the organic layer. The isolated compound can also be purified by chromatography, recrystallization, and the like.

(Reference Production Process A)

The compound (A2) can be produced by reacting the compound (AA2) with a sulfurizing agent:

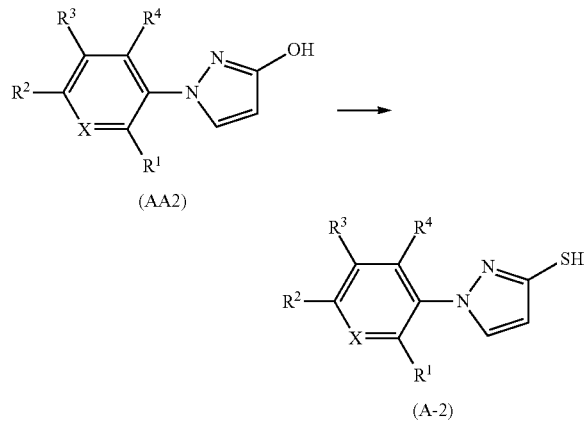

wherein symbols are the same as defined above.

The reaction is usually performed in a solvent.

Examples of the solvent to be used in the reaction include hydrocarbons such as toluene and xylene; ethers such as tetrahydrofuran, 1,4-dioxane, ethylene glycol dimethyl ether, and anisole; acid amides such as N,N-dimethylformamide, 1,3-dimethyl-2-imidazolidinone, and N-methylpyrrolidone; nitriles such as acetonitrile; mixtures thereof, and mixtures of water and these solvents.

Examples of the sulfurizing agent to be used in the reaction include phosphorous pentasulfide, Lawesson's reagent (2,4-bis(4-methoxyphenyl)-1,3,2,4-dithiadiphosphetane-2,4-disulfide), and the like.

In the reaction, the sulfurizing agent is usually used in the proportion within a range of 0.5 to 10 mols based on 1 mol of the compound (AA2).

The reaction temperature of the reaction is usually within a range of 20 to 250° C. The reaction time of the reaction is usually within a range of 0.1 to 50 hours.

After completion of the reaction, the compound (A2) can be isolated by performing post-treatment operations such as extraction of the reaction mixture with an organic solvent, and drying and concentration of the organic layer. The isolated compound (A2) can also be purified by chromatography, recrystallization, and the like.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyoxyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenoland3-tert-butyl-4-methoxyphenol), vegetable oils, mineral oils, fatty acids or fatty acid esters thereof, and the like.

The method for applying the present control agent is not particularly limited, as long as the applying form is a form by which the present control agent can be applied substantially, and includes, for example, an application to plants such as a foliage application; an application to area for cultivating plants such as a submerged treatment; and an application to seeds such as seed disinfection.

The present control agent may be used as a mixture with various oils such as mineral oils or vegetable oils or surfactants. Specific examples of oils or surfactants, which can be used as a mixture with various oils or surfactants include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITONX 45 (registered trademark), AGRAL 90 (registered trademark), AGROTIN (registered trademark), ARPON (registered trademark), EnSpray N (registered trademark), BANOLE (registered trademark), and the like.

The present compound can also be used as a mixture with other fungicides, insecticides, acaricides, nematicides, and plant growth regulators, or simultaneously therewith.

The application dose of the present control agent varies depending on weather conditions, dosage forms, timing of application, methods of application, areas to be applied, target diseases, target plants, and the like, and the amount of the present compound in the present control agent is usually within a range of 1 to 500 g, and preferably 2 to 200 g, per 1,000 m$^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound in the present control agent is usually within a range of 0.001 to 100 g, and preferably 0.01 to 50 g, per 1 kg of the seeds.

Also, in another embodiment, for example, the present compound or the present control agent can be administered to the inside (inside of the body) or the outside (body surface) of the below-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly, or intravenously. Examples of a method of the external administration include transdermal administration. Also, the present compound can be ingested to a livestock animal so as to exterminate sanitary insects which occur in the excrement of the animal.

When the present compound or the present control agent is applied to the animals such as the livestock animal and pets on which pests are parasitic, the dose varies depending on the administration method etc., and it is desirable to administer the present compound so that a dose of the active ingredient (present compound) is generally within a range of 0.1 mg to 2,000 mg, and preferably 0.5 mg to 1,000 mg, per 1 kg of body weight of the animal.

The present compound or the present control agent can be used as an agent for controlling plant diseases in agricultural lands such as fields, paddy fields, lawns, and orchards. The present compound can control diseases occurred in the agricultural lands for cultivating the following plants.

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica*, colocasia, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like;

Trees other than fruit trees: tea, mulberry, flowering plant, roadside trees (for example, ash, birch, dogwood, Eucalyptus, Ginkgo biloba, lilac, maple, Quercus, poplar, Judas tree, *Liquidambar formosana*, plane tree, zelkova, Japanese arborvitae, fir wood, hemlock, juniper, Pinus, Picea, and *Taxus cuspidate*); and the like.

The above-mentioned plants include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), damping-off by *Rhizoctonia* (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by *Rhizoctonia* (*Rhizoctonia solani*); Corn diseases: rust (*Puccinia sorghi*), southern rust (*Puccinia polysora*), northern leaf blight (*Setosphaeriaturcica*), southern leaf blight (*Cochliobolus heterostrophus*), anthracnose (*Colletotrichum graminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramularia areola*), and alternaria leaf spot (*Alternaria macrospora, A. gossypii*); Coffee diseases: rust (*Hemileia vastatrix*); Rape seed diseases: *sclerotinia* rot (*Sclerotinia sclerotiorum*), black spot (*Alternaria brassicae*), and black leg (*Phomalingam*); Citrus diseases: melanose (*Diaporthecitri*), scab (*Elsinoe fawcetti*), and fruit rot (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.);Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardiabidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia aerial blight (*Rhizoctonia solani*), septoria brown spot (*Septoria* glycines), and frog eye leaf spot (*Cercospora sojina*); Kidney bean diseases: anthracnose (*Colletotrichum lindemuthianum*); Peanut diseases: early leaf spot (*Cercospora personata*), late leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: *cercospora* leaf spot (*Cercospora beticola*), leaf blight (*Thanatephorus cucumeris*), root rot (*Thanatephorus cucumeris*), and aphanomyces root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytiscinerea, B. byssoidea, B. squamosa*), gray-mold neck rot (*Botrytis alli*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (Myzuspersicae), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lice (*Homoptera, Psylloidea*); and bed bugs (*Cimex lectularius*).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*).

*Diptera:* houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

*Coleoptera:* twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

*Orthoptera:* asiatic locusts (*Locusta migratoria*), African mole cricket (*Gryllotalpa africana*), rice grasshopper (*Oxya yezoensis*), and rice grasshopper (*Oxya japonica*).

*Hymenoptera:* cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides pteronyssinus*)); Cheyletidae (for example, cheyletid mite (*Cheyletus eruditus*), *Cheyletus malaccensis*, and *Cheyletus moorei;* and Dermanyssidae.

The formulation comprising the present compound can be used in the field relating to a treatment of livestock diseases or livestock industry, and can exterminate the living things or parasites which are parasitic on the inside and/or the outside of vertebrates such as human being, cow, sheep, goat, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenopsylla* spp., Pharaoh's ant (*Monomorium pharaonis*) and nematodes [for example, hairworm (for example, *Nippostrongylus brasiliensis, Trichostrongylus axei, Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta, Cooperia* spp., *Hymenolepis nana*, and the like.

The present control agent containing at least one selected from the group consisting of the above-mentioned known fungicides, insecticide, acaricides, nematicides, and plant growth regulators may be directly applied to a plant body to be protected from pests, or may be applied to soil for fix planting of the plant body, and seeds.

At least one selected from the group consisting of the above-mentioned known fungicides, insecticide, acaricides, nematicides, and plant growth regulators may be applied to the plant body, simultaneously or separately, when using together with the present control agent. When applying separately, an application date may be different and a different dosage form may be used.

It is possible to combine an application of the present control agent to seeds of the plant with an application of at least one selected from the group consisting of the above-mentioned known fungicides, insecticide, acaricides, nematicides, and plant growth regulators to the plant, or soil for fix planting of the plant. It is also possible to combine an application of at least one selected from the group consisting of known fungicides, insecticide, acaricides, nematicides, and plant growth regulators to seeds of the plant with an application of the present control agent to the plant, or soil for fix planting of the plant. An application to the plant, or soil for fix planting of the plant may be performed before, on, or after fix planting.

This application method is preferably applied to cultivation of corn, wheat, and rice.

It is possible to combine an application of the present control agent to a plant body, or soil on which the plant body is cultivated or to be cultivated (for example, soil of paddy fields, crop fields, orchards, or non-cultivated lands) with an application of at least one selected from known herbicides to the soil. The pest control agent of the present invention and herbicides can be applied simultaneously or separately. When applying separately, the application maybe performed on the same or different day.

Examples of the herbicide, which can be used together with the present control agent, include glyphosate, salts of glyphosate, glufosinate, salts of glyphosate, 2,4-D, salts of 2,4-D, dicamba, salts of dicamba, and flumioxazin.

EXAMPLES

The present invention will be described in more detail below by way of Production Examples, Formulation Examples, and Test Examples, but the present invention is not limited to these Examples.

First, Production Examples will be described.

Production Example 1

A mixture of 3 g 1-(4-chlorophenyl)-1H-pyrazol-3-ol (produced in accordance with WO 2013/162072 A), 10.3 g of di-phosphorus pentasulfide, and 100 ml of xylene was stirred at 150° C. for 24 hours. The reaction mixture was concentrated under reduced pressure. The residue thus obtained was diluted with ethyl acetate and then filtered through silica gel. The filtrate was concentrated under reduced pressure to obtain 1.17 g of a crude product containing 1-(4-chlorophenyl)-1H-pyrazole-3-thiole. A mixture of 1.10 g of 1-(2-bromomethyl-3-methylphenyl)-4-methyl-1,4-dihydrotetrazol-5-one (produced in accordance with WO 2013/162072A), 1.17 g of the crude product containing 1-(4-chlorophenyl)-1H-pyrazole-3-thiole, 2.09 g of potassium carbonate, and 10 ml of acetonitrile was stirred at 80° C. for 12 hours. The reaction mixture was concentrated under reduced pressure. The residue thus obtained was subjected to silica gel column chromatography to obtain 0.50 g of 1-(2-{[1-(4-chlorophenyl)-1H-pyrazol-3-yl]thiomethyl}-3-methylphenyl)-4-methyl-1,4-dihydrotetrazol-5-one (hereinafter referred to as the present compound 1).

Present Compound 1

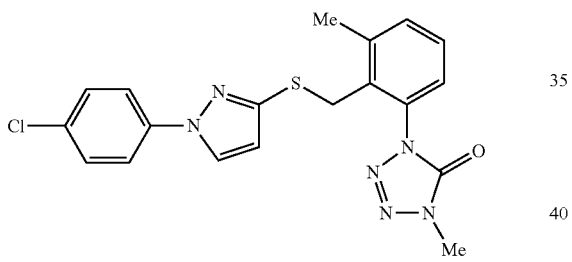

$^1$H-NMR (CDCl$_3$) δ: 7.74 (1H, d, J=2.5 Hz), 7.58 (2H, dt, J=9.5, 2.6 Hz), 7.41 (2H, dt, J=9.4, 2.5 Hz), 7.34-7.30 (1H, m), 7.28 (1H, d, J=7.6 Hz), 7.15 (1H, d, J=7.3 Hz), 6.19 (1H, d, J=2.5 Hz), 4.33 (2H, s), 3.53 (3H, s), 2.47 (3H, s).

In accordance with the process mentioned above, it is possible to obtain compounds HA1001-001 to HA1012-333. The above-mentioned compounds HA1001-001 to HA1012-333 (hereinafter referred to as the present compound A) are aromatic compounds shown below [wherein Q represents any one of the below-mentioned substituent numbers 1 to 333]. In the following [substituent number; Q], 3-Py represents pyridin-3-yl, Ph represents phenyl, F represents fluoro, Cl represents chloro, Br represents bromo, CN represents cyano, Me represents methyl, Et represents ethyl, Pr represents propyl, i-Pr represents isopropyl, CF3 represents trifluoromethyl, OMe represents methoxy, OEt represents ethoxy, OPr represents propoxy, Oi-Pr represents isopropoxy, di represents di, and tri represents tri.

HA1006-006 represents a group in which Q is represented by the substituent number 006 in formula (HA1006), and specifically represents a compound represented by the following formula.

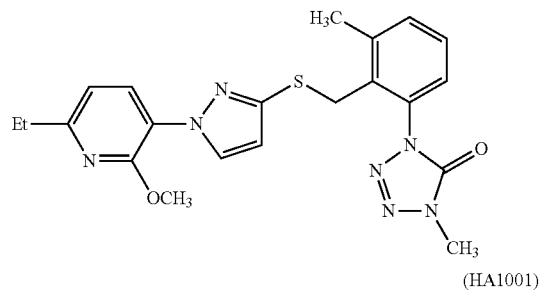
(HA1001)

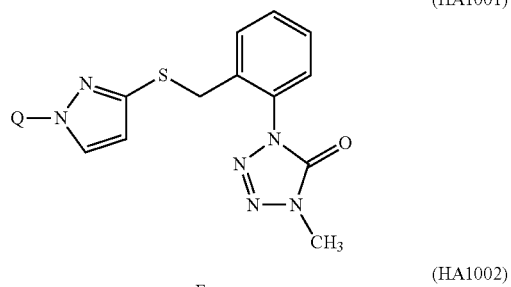
(HA1002)

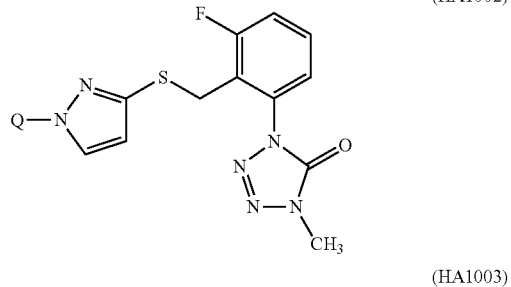
(HA1003)

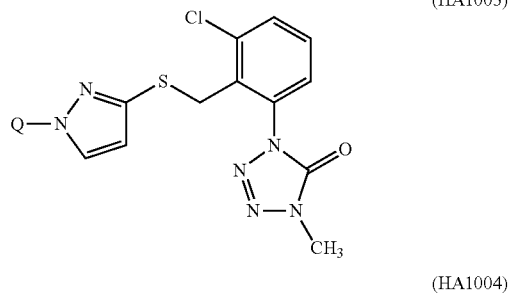
(HA1004)

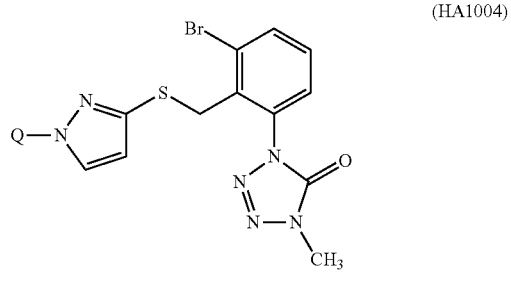
(HA1005)

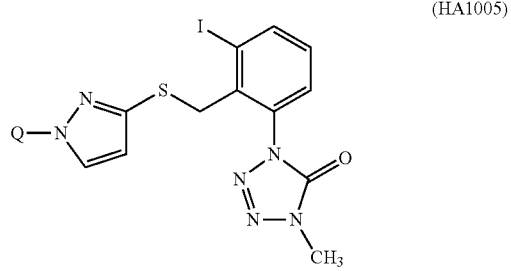

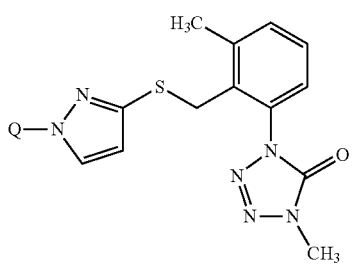 (HA1006)

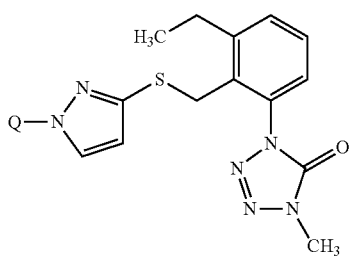 (HA1007)

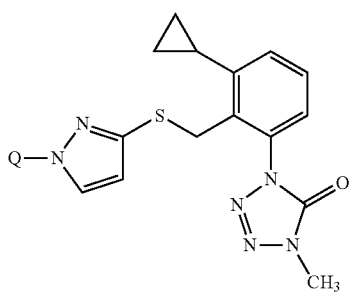 (HA1008)

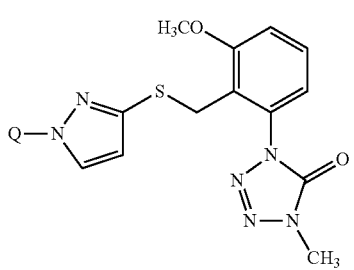 (HA1009)

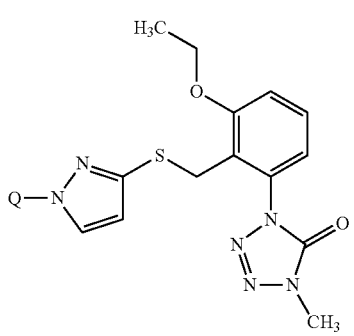 (HA1010)

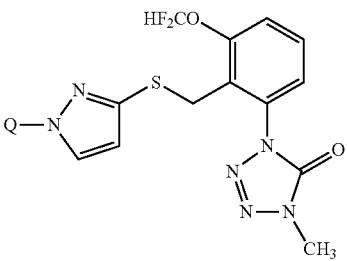 (HA1011)

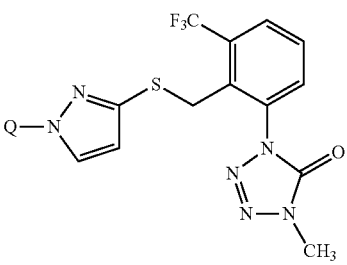 (HA1012)

[substituent number: Q], [001:2-OMe-3-Py], [002:6-F-2-OMe-3-Py], [003:6-Cl-2-OMe-3-Py], [004:6-Br-2-OMe-3-Py], [005:6-Me-2-OMe-3-Py], [006:6-Et-2-OMe-3-Py], [007:6-Pr-2-OMe-3-Py], [008:6-i-Pr-2-OMe-3-Py], [009:6-CN-2-OMe-3-Py], [010:6-CF3-2-OMe-3-Py], [011:2,6-diOMe-3-Py], [012:6-OEt-2-OMe-3-Py], [013:6-OPr-2-OMe-3-Py], [014:6-i-OPr-2-OMe-3-Py], [015:4-F-2-OMe-3-Py], [016:4,6-diF-2-OMe-3-Py], [017:4-F-6-Cl-2-OMe-3-Py], [018:4-F-6-Br-2-OMe-3-Py], [019:4-F-6-Me-2-OMe-3-Py], [020:4-F-6-Et-2-OMe-3-Py], [021:4-F-6-Pr-2-OMe-3-Py], [022:4-F-6-i-Pr-2-OMe-3-Py], [023:4-F-6-CN-2-OMe-3-Py], [024:4-F-6-CF3-2-OMe-3-Py], [025:4-F-2,6-diOMe-3-Py], [026:4-F-6-OEt-2-OMe-3-Py], [027:4-F-6-OPr-2-OMe-3-Py], [028:4-F-6-i-OPr-2-OMe-3-Py], [029:4-Cl-2-OMe-3-Py], [030:4-Cl-6-F-2-OMe-3-Py], [031:4,6-diCl-2-OMe-3-Py], [032:4-Cl-6-Br-2-OMe-3-Py], [033:4-Cl-6-Me-2-OMe-3-Py], [034:4-Cl-6-Et-2-OMe-3-Py], [035:4-Cl-6-Pr-2-OMe-3-Py], [036:4-Cl-6-i-Pr-2-OMe-3-Py], [037:4-Cl-6-CN-2-OMe-3-Py], [038:4-Cl-6-CF3-2-OMe-3-Py], [039:4-Cl-2,6-diOMe-3-Py], [040:4-Cl-6-OEt-2-OMe-3-Py], [041:4-Cl-6-OPr-2-OMe-3-Py], [042:4-Cl-6-i-OPr-2-OMe-3-Py], [043:2,4-diOMe-3-Py], [044:6-F-2,4-diOMe-3-Py], [045:6-Cl-2,4-diOMe-3-Py], [046:6-Br-2,4-diOMe-3-Py], [047:6-Me-2,4-diOMe-3-Py][048:6-Et-2,4-diOMe-3-Py], [049:6-Pr-2,4-diOMe-3-Py], [050:6-i-Pr-2,4-diOMe-3-Py], [051:6-CN-2,4-diOMe-3-Py], [052:6-CF3-2,4-diOMe-3-Py], [053:2,4,6-triOMe-3-Py], [054:6-OEt-2,4-diOMe-3-Py], [055:6-OPr-2,4-diOMe-3-Py], [056:6-i-OPr-2,4-diOMe-3-Py], [057:5-F-2-OMe-3-Py], [058:5,6-diF-2-OMe-3-Py], [059:5-F-6-Cl-2-OMe-3-Py], [060:5-F-6-Br-2-OMe-3-Py], [061:5-F-6-Me-2-OMe-3-Py], [062:5-F-6-Et-2-OMe-3-Py], [063:5-F-6-Pr-2-OMe-3-Py], [064:5-F-6-i-Pr-2-OMe-3-Py], [065:5-F-6-CN-2-OMe-3-Py], [066:5-F-6-CF3-2-OMe-3-Py], [067:5-F-2,6-diOMe-3-Py], [068:5-F-6-O Et-2-OMe-3-Py], [069:5-F-6-OPr-2-OMe-3-Py], [070:5-F-6-i-OPr-2-OMe-3-Py], [071:4,5-diF-2-OMe-3-Py], [072:4,5,6-triF-2-OMe-3-Py], [073:4,5-diF-6-Cl-2-OMe-3-Py], [074:4,5-diF-6-Br-2-OMe-3-Py], [075:4,5-diF-6-Me-2-OMe-3-Py], [076:4,5-diF-6-Et-2-OMe-3-Py], [077:4,5-diF-6-Pr-2-OMe-3-Py], [078:4,5-diF-6-i-Pr-2-OMe-3-Py], [079:4,5-diF-6-CN-2-OMe-3-Py], [080:4,5-diF-6-CF3-2-OMe-3-Py],

[081:4,5-diF-2,6-diOMe-3-Py], [082:4,5-diF-6-OEt-2-OMe-3-Py], [083:2-OEt-3-Py], [084:6-F-2-OEt-3-Py], [085:6-Cl-2-OEt-3-Py], [086:6-Br-2-OEt-3-Py], [087:6-Me-2-OEt-3-Py], [088:6-Et-2-OEt-3-Py], [089:6-Pr-2-OEt-3-Py], [090:6-i-Pr-2-OEt-3-Py], [091:6-CN-2-OEt-3-Py], [092:6-CF3-2-OEt-3-Py], [093:6-OMe-2-OEt-3-Py], [094:2,6-diOEt-3-Py], [095:6-OPr-2-OEt-3-Py], [096:6-i-OPr-2-OEt-3-Py], [097:4-F-2-OEt-3-Py], [098:4,6-diF-2-OEt-3-Py], [099:4-F-6-Cl-2-OEt-3-Py], [100:4-F-6-Br-2-OEt-3-Py],

[101:4-F-6-Me-2-OEt-3-Py], [102:4-F-6-Et-2-OEt-3-Py], [103:4-F-6-Pr-2-OEt-3-Py], [104:4-F-6-i-Pr-2-OEt-3-Py], [105:4-F-6-CN-2-OEt-3-Py], [106:4-F-6-CF3-2-OEt-3-Py], [107:4-F-6-OMe-2-OEt-3-Py], [108:4-F-2,6-diOEt-3-Py], [109:4-F-6-OPr-2-OEt-3-Py], [110:4-F-6-i-OPr-2-OEt-3-Py], [111:4-Cl-2-OEt-3-Py], [112:4-Cl-6-F-2-OEt-3-Py], [113:4,6-diCl-2-OEt-3-Py], [114:4-Cl-6-Br-2-OEt-3-Py], [115:4-Cl-6-Me-2-OEt-3-Py], [116:4-Cl-6-Et-2-OEt-3-Py], [117:4-Cl-6-Pr-2-OEt-3-Py], [118:4-Cl-6-i-Pr-2-OEt-3-Py], [119:4-Cl-6-CN-2-OEt-3-Py], [120:4-Cl-6-CF3-2-OEt-3-Py], [121:4-Cl-6-OMe-2-OEt-3-Py], [122:4-Cl-2,6-diOEt-3-Py], [123:4-Cl-6-OPr-2-OEt-3-Py], [124:4-Cl-6-i-OPr-2-OEt-3-Py], [125:4-OMe-2-OEt-3-Py], [126:6-F-4-OMe-2-OEt-3-Py], [127:6-Cl-4-OMe-2-OEt-3-Py], [128:6-Br-4-OMe-2-OEt-3-Py], [129:6-Me-4-OMe-2-OEt-3-Py][130:6-Et-4-OMe-2-OEt-3-Py], [131:6-Pr-4-OMe-2-OEt-3-Py], [132:6-i-Pr-4-OMe-2-OEt-3-Py], [133:6-CN-4-OMe-2-OEt-3-Py], [134:6-CF3-4-OMe-2-OEt-3-Py], [135:2,6-diOMe-2-OEt-3-Py], [136:4-OMe-2,6-diOEt-3-Py], [137:6-OPr-4-OMe-2-OEt-3-Py], [138:6-i-OPr-4-OMe-2-OEt-3-Py], [139:5-F-2-OEt-3-Py], [140:5,6-diF-2-OEt-3-Py], [141:5-F-6-Cl-2-OEt-3-Py], [142:5-F-6-Br-2-OEt-3-Py], [143:5-F-6-Me-2-OEt-3-Py], [144:5-F-6-Et-2-OEt-3-Py], [145:5-F-6-Pr-2-OEt-3-Py], [146:5-F-6-i-Pr-2-OEt-3-Py], [148:5-F-6-CN-2-OEt-3-Py], [150:5-F-6-CF3-2-OEt-3-Py], [151:5-F-6-OMe-2-OEt-3-Py], [152:5-F-2,6-diOEt-3-Py], [153:5-F-6-OPr-2-OEt-3-Py], [154:5-F-6-i-OPr-2-OEt-3-Py], [155:4,5-diF-2-OEt-3-Py], [156:4,5,6-triF-2-OEt-3-Py], [157:4,5-diF-6-Cl-2-OEt-3-Py], [158:4,5-diF-6-Br-2-OEt-3-Py], [159:4,5-diF-6-Me-2-OEt-3-Py], [160:4,5-diF-6-Et-2-OEt-3-Py], [161:4,5-diF-6-Pr-2-OEt-3-Py], [162:4,5-diF-6-i-Pr-2-OEt-3-Py], [163:4,5-diF-6-CN-2-OEt-3-Py], [164:4,5-diF-6-CF3-2-OEt-3-Py], [165:4,5-diF-6-OMe-2-OEt-3-Py], [166:4,5-diF-2,6-diOEt-3-Py], [167:2-OMe-Ph], [168:4-F-2-OMe-Ph], [169:4-Cl-2-OMe-Ph], [170:4-Br-2-OMe-Ph], [171:4-Me-2-OMe-Ph], [172:4-Et-2-OMe-Ph], [173:4-Pr-2-OMe-Ph], [174:4-i-Pr-2-OMe-Ph], [175:4-CN-2-OMe-Ph], [176:4-CF3-2-OMe-Ph], [177:2,4-diOMe-Ph], [178:4-OEt-2-OMe-Ph], [179:4-OPr-2-OMe-Ph], [180:4-i-OPr-2-OMe-Ph], [181:6-F-2-OMe-3-Py], [182:4,6-diF-2-OMe-Ph], [183:4-F-4-Cl-2-OMe-Ph], [184:6-F-4-Br-2-OMe-Ph], [185:6-F-4-Me-2-OMe-Ph], [186:6-F-4-Et-2-OMe-Ph], [187:6-F-4-Pr-2-OMe-Ph], [188:6-F-4-i-Pr-2-OMe-Ph], [189:6-F-4-CN-2-OMe-Ph], [190:6-F-4-CF3-2-OMe-Ph], [191:6-F-2,4-diOMe-Ph], [192:6-F-4-OEt-2-OMe-Ph], [193:6-F-4-OPr-2-OMe-Ph], [194:6-F-4-i-OPr-2-OMe-Ph], [195:6-Cl-4-OMe-Ph], [196:6-Cl-4-F-2-OMe-Ph], [197:4,6-diCl-2-OMe-Ph], [198:6-Cl-4-Br-2-OMe-Ph], [199:6-Cl-4-Me-2-OMe-Ph], [200:6-Cl-4-Et-2-OMe-Ph],

[201:6-Cl-4-Pr-2-OMe-Ph], [202:6-Cl-4-i-Pr-2-OMe-Ph], [203:6-Cl-4-CN-2-OMe-Ph], [204:6-Cl-4-CF3-2-OMe-Ph], [205:6-Cl-2,4-diOMe-Ph], [206:6-Cl-4-OEt-2-OMe-Ph], [207:6-Cl-4-OPr-2-OMe-Ph], [208:6-Cl-4-i-OPr-2-OMe-Ph], [209:2,6-diOMe-Ph], [210:4-F-2,6-diOMe-Ph], [211:4-Cl-2,6-diOMe-Ph], [212:4-Br-2,6-diOMe-Ph], [213:4-Me-2,6-diOMe-Ph][214:4-Et-2,6-diOMe-Ph], [215:4-Pr-2,6-diOMe-Ph], [216:4-i-Pr-2,6-diOMe-Ph], [217:4-CN-2,6-diOMe-Ph], [218:4-CF3-2,6-diOMe-Ph], [219:2,4,6-triOMe-Ph], [220:4-OEt-2,6-diOMe-Ph], [221:4-OPr-2,6-diOMe-Ph], [222:4-i-OPr-2,6-diOMe-Ph], [223:5-F-2-OMe-Ph], [224:4,5-diF-2-OMe-Ph], [225:5-F-4-Cl-2-OMe-Ph], [226:5-F-4-Br-2-OMe-Ph], [227:5-F-4-Me-2-OMe-Ph], [228:5-F-4-Et-2-OMe-Ph], [229:5-F-4-Pr-2-OMe-Ph], [230:5-F-4-i-Pr-2-OMe-Ph], [231:5-F-4-CN-2-OMe-Ph], [232:5-F-4-CF3-2-OMe-Ph], [233:5-F-2,4-diOMe-Ph], [234:5-F-4-OEt-2-OMe-Ph], [235:5-F-4-OPr-2-OMe-Ph], [236:5-F-4-i-OPr-2-OMe-Ph], [237:5,6-diF-2-OMe-Ph], [238:4,5,6-triF-2-OMe-Ph], [239:5,6-diF-4-Cl-2-OMe-Ph], [240:5,6-diF-4-Br-2-OMe-Ph], [241:5,6-diF-4-Me-2-OMe-Ph], [242:5,6-diF-4-Et-2-OMe-Ph], [243:5,6-diF-4-Pr-2-OMe-Ph], [244:5,6-diF-4-i-Pr-2-OMe-Ph], [245:5,6-diF-4-CN-2-OMe-Ph], [246:5,6-diF-4-CF3-2-OMe-Ph], [247:5,6-diF-2,4-diOMe-Ph], [248:5,6-diF-4-OEt-2-OMe-Ph], [249:2-OEt-Ph], [250:4-F-2-OEt-Ph], [251:4-Cl-2-OEt-Ph], [252:4-Br-2-OEt-Ph], [253:4-Me-2-OEt-Ph], [254:4-Et-2-OEt-Ph], [255:4-Pr-2-OEt-Ph], [256:4-i-Pr-2-OEt-Ph], [257:4-CN-2-OEt-Ph], [258:4-Ac-2-OEt-Ph], [259:4-CF3-2-OEt-Ph], [260:4-OMe-2-OEt-Ph], [261:2,4-diOEt-Ph], [262:4-OPr-2-OEt-Ph], [263:4-i-OPr-2-OEt-Ph], [264:6-F-2-OEt-Ph], [265:4,6-diF-2-OEt-Ph], [266:6-F-4-Cl-2-OEt-Ph], [267:6-F-4-Br-2-OEt-Ph], [268:6-F-4-Me-2-OEt-Ph], [269:6-F-4-Et-2-OEt-Ph], [270:6-F-4-Pr-2-OEt-Ph], [271:6-F-4-i-Pr-2-OEt-Ph], [272:6-F-4-CN-2-OEt-Ph], [273:6-F-4-CF3-2-OEt-Ph], [274:6-F-4-OMe-2-OEt-3-Ph], [275:6-F-2,4-diOEt-Ph], [276:6-F-4-OPr-2-OEt-Ph], [277:6-F-4-i-OPr-2-OEt-Ph], [278:6-Cl-2-OEt-Ph], [279:6-Cl-4-F-2-OEt-Ph], [280:4,6-diCl-2-OEt-Ph], [281:6-Cl-4-Br-2-OEt-Ph], [282:6-Cl-4-Me-2-OEt-Ph], [283:6-Cl-4-Et-2-OEt-Ph], [284:6-Cl-4-Pr-2-OEt-Ph], [285:6-Cl-4-i-Pr-2-OEt-Ph], [286:6-Cl-4-CN-2-OEt-Ph], [287:6-Cl-4-CF3-2-OEt-Ph], [288:6-Cl-4-OMe-2-OEt-Ph], [289:6-Cl-2,4-diOEt-Ph], [290:6-Cl-4-OPr-2-OEt-Ph], [291:6-Cl-4-i-OPr-2-OEt-Ph], [292:6-OMe-2-OEt-Ph], [293:4-F-6-OMe-2-OEt-Ph], [294:4-Cl-6-OMe-2-OEt-Ph], [295:4-Br-6-OMe-2-OEt-Ph], [296:4-Me-6-OMe-2-OEt-Ph][297:4-Et-6-OMe-2-OEt-Ph], [298:4-Pr-6-OMe-2-OEt-Ph], [299:4-i-Pr-6-OMe-2-OEt-Ph], [300:4-CN-6-OMe-2-OEt-Ph],

[301:4-CF3-6-OMe-2-OEt-Ph], [302:4,6-diOMe-2-OEt-Ph], [303:6-OMe-2,4-diOEt-Ph], [304:4-OPr-6-OMe-2-OEt-Ph], [305:4-i-OPr-6-OMe-2-OEt-Ph], [306:5-F-2-OEt-Ph], [307:4,5-diF-2-OEt-Ph], [308:5-F-4-Cl-2-OEt-Ph], [309:5-F-4-Br-2-OEt-Ph], [310:5-F-4-Me-2-OEt-Ph], [311:5-F-4-Et-2-OEt-Ph], [312:5-F-4-Pr-2-OEt-Ph], [313:5-F-4-i-Pr-2-OEt-Ph], [314:5-F-4-CN-2-OEt-Ph], [315:5-F-4-CF3-2-OEt-Ph], [316:5-F-4-OMe-2-OEt-Ph], [317:5-F-2,4-diOEt-Ph], [318:5-F-4-OPr-2-OEt-Ph], [319:5-F-4-i-OPr-2-OEt-Ph], [320:5,6-diF-2-OEt-Ph], [321:4,5,6-triF-2-OEt-Ph], [322:5,6-diF-4-Cl-2-OEt-Ph], [323:5,6-diF-4-Br-2-OEt-Ph], [324:5,6-diF-4-Me-2-OEt-Ph], [325:5,6-diF-4-Et-2-OEt-Ph], [326:5,6-diF-4-Pr-2-OEt-Ph], [327:5,6-diF-4-i-Pr-2-OEt-Ph], [328:5,6-diF-4-CN-2-OEt-Ph], [329:5,6-diF-4-CF3-2-OEt-Ph], [330:5,6-diF-4-OMe-2-OEt-Ph], [331:5,6-diF-2,4-diOEt-Ph], [332:Ph], [333:3-Py]

Formulation Examples will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water are mixed and finely ground by a wet grinding method to obtain each formulation.

Next, Test Examples will be shown.

Test Example 1

Each of plastic pots was filled with soil and barley (cultivar: MIKAMO GOLDEN) was sowed and grown in a greenhouse for 7 days. Then, each water dilution prepared by adjusting so as to contain a predetermined concentration (500 ppm) of the present compound 1 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with of the present compound was 30% or less of that on an untreated plant.

Test Example 2

Each of plastic pots was filled with soil and kidney bean (cultivar: NAGAUZURA SAITOU) was sowed and grown in a greenhouse for 8 days. Then, each water dilution prepared by adjusting so as to contain a predetermined concentration (500 ppm) of the present compound 1 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound was 30% or less of that on an untreated plant.

Test Example 3

Each of plastic pots was filled with soil and wheat (cultivar: APOGEE) was sowed and grown in a greenhouse for 10 days. Then, each water dilution prepared by adjusting so as to contain a predetermined concentration (500 ppm) of the present compound 1 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed over the wheat to inoculate the spores. After completion of the inoculation, the plant was placed at 18° C. under high humidity condition for 3 days and then placed under illumination for 14 to 18 days, and then the area of lesion was investigated. As a result, the area of lesion on the plant treated with the present compound was 30% or less of that on an untreated plant.

Test Example 4

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of the present compound 1 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*, a QoI-resistant strain in which, among the genes encoding cytochrome b, the amino acid residue at position 143 of cytochrome b is mutated from glycine to alanine). After the inoculation, the plant was cultivated in a greenhouse at 24° C. in the daytime and 20° C. at night for 8 days, and then the area of lesion was investigated. As a result, the area of lesion on the plant treated with the present compound was 30% or less of that on an untreated plant.

Test Example 5

Each of plastic pots was filled with soil and wheat (cultivar: SHIROGANE) was sowed and grown in a greenhouse for 9 days. Then, each water dilution prepared by adjusting so as to contain a predetermined concentration (200 ppm) of the present compound 1 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, the area of lesion on the plant treated with the present compound was 30% or less of that on an untreated plant.

Test Example 6

Each of plastic pots was filled with soil and barley (cultivar: MIKAMO GOLDEN) was sowed and grown in a greenhouse for 7 days. Then, each water dilution prepared by adjusting so as to contain a predetermined concentration (200 ppm) of the present compound 1 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with of the present compound was 30% or less of that on an untreated plant.

Test Example 7

Each of plastic pots was filled with soil and cucumber (cultivar: SAGAMI HANJIRO) was sowed and grown in a greenhouse for 19 days. Then, each water dilution prepared by adjusting so as to contain a predetermined concentration (50 ppm) of the present compound 1 was sprayed over stems and leaves of the cucumber so that it sufficiently adhered to the surface of the leaves of the cucumber. After spraying, the plant was air-dried and then, after 1 day, an aqueous suspension containing spores of cucumber anthracnose fungus (*Colletotrichum lagenarium*) was sprayed to inoculate the spores. After the inoculation, the plant was placed at 23° C. for one day under high humidity condition, and then cultivated in a greenhouse at 24° C. in the daytime and 20° C. at night for 6 days, and then the area of lesion was investigated. As a result, the area of lesion on the plant treated with the present compound was 30% or less of that on an untreated plant.

Test Example 8

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of the present compound 1 was sprayed over stems and leaves of the cucumber so that it sufficiently adhered to the surface of the leaves of the cucumber. After spraying, the plant was air-dried and then, after 1 day, an aqueous suspension containing zoospores of cucumber downy mildew fungus (*Pseudoperonospora cubensis*) was sprayed to inoculate the zoospores. After the inoculation, the plant was placed stand at 23° C. for one day under high humidity condition, and then cultivated in a greenhouse at 24° C. in the daytime and 20° C. at night for 6 days, and then the area of lesion was investigated. As a result, the area of lesion on the plant treated with the present compound was 30% or less of that on an untreated plant.

The present compound has control activity against pests and is useful as an active ingredient of a pest control agent.

The invention claimed is:
1. A tetrazolinone compound represented by formula (1):

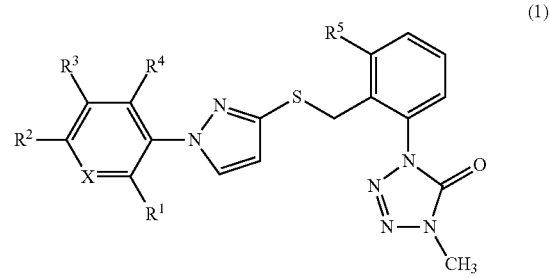

wherein X represents a nitrogen atom,
$R^1$, $R^2$, $R^3$, and $R^4$ each independently represents a halogen atom, a hydrogen atom, a cyano group, a C1-C4 alkyl group optionally substituted with one or more halogen atoms, or a C1-C4 alkoxy group optionally substituted with one or more halogen atoms, and
$R^5$ represents a halogen atom, a C1-C4 alkyl group optionally substituted with one or more halogen atoms, a C3-C4 cycloalkyl group optionally substituted with one or more halogen atoms, or a C1-C4 alkoxy group optionally substituted with one or more halogen atoms.

2. The tetrazolinone compound according to claim 1, wherein $R^3$ and $R^4$ are hydrogen atoms.

3. A pest control agent comprising the tetrazolinone compound according to claim 1.

4. A pest control agent comprising the tetrazolinone compound according to claim 2.

5. A method for controlling pests, which comprises applying an effective amount of the tetrazolinone compound according to claim 1 to plants or soil.

6. A method for controlling pests, which comprises applying an effective amount of the tetrazolinone compound according to claim 2 to plants or soil.

* * * * *